United States Patent [19]

Berg

[11] Patent Number: 5,876,569

[45] Date of Patent: Mar. 2, 1999

[54] SEPARATION OF METHYL ETHYL KETONE FROM ETHANOL BY EXTRACTIVE DISTILLATION

[76] Inventor: Lloyd Berg, 1314 S. 3rd Ave., Bozeman, Mont. 59715

[21] Appl. No.: 106,407

[22] Filed: Jun. 29, 1998

[51] Int. Cl.⁶ .............................. B01D 3/40; C07C 27/32; C07C 45/83

[52] U.S. Cl. .................. 203/57; 203/58; 203/59; 203/60; 203/62; 203/63; 203/64; 203/65; 203/67; 203/69; 203/70; 568/410; 568/913

[58] Field of Search .................. 203/57, 58–60, 203/62–65, 67, 69–70; 568/410, 913

[56] References Cited

U.S. PATENT DOCUMENTS

| | | | |
|---|---|---|---|
| 4,113,780 | 9/1978 | Strehlke et al. ........................ | 203/62 |
| 4,428,798 | 1/1984 | Zudkevitch et al. ...................... | 203/65 |
| 4,431,838 | 2/1984 | Feldman et al. ......................... | 203/69 |
| 4,447,643 | 5/1984 | Feldman ................................ | 568/916 |
| 4,459,178 | 7/1984 | Berg et al. ............................. | 203/60 |
| 4,470,881 | 9/1984 | Berg .................................... | 203/64 |
| 4,501,645 | 2/1985 | Berg et al. ............................. | 203/60 |
| 4,544,454 | 10/1985 | Berg et al. ............................. | 203/57 |
| 4,584,063 | 4/1986 | Berg et al. ............................. | 203/60 |
| 5,348,625 | 9/1994 | Berg .................................... | 203/58 |
| 5,470,443 | 11/1995 | Berg .................................... | 203/65 |

*Primary Examiner*—Virginia Manoharan

[57] ABSTRACT

Methyl ethyl ketone cannot be separated from ethanol by distillation or rectification because of the closeness of their boiling points. Methyl ethyl ketone is readily separated from ethanol by extractive distillation. Effective agents are methyl benzoate, phenol, glycerol and nitroethane.

2 Claims, No Drawings

SEPARATION OF METHYL ETHYL KETONE FROM ETHANOL BY EXTRACTIVE DISTILLATION

FIELD OF THE INVENTION

This invention relates to a method For separating methyl ethyl ketone from ethanol using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and base separation, or solvent extraction.

TABLE 1

Effect of Relative Volatility on Theoretical Stage Requirements.

| Separation Purity | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

Methyl ethyl ketone and ethanol boil only one degree apart and have a relative volatility of 1.1 which makes it impossible to separate them by conventional distillation or rectification. Table 2 shows that with an agent giving a relative volatility of 1.65, only 26 actual-plates are required to get 99% purity.

TABLE 2

Theoretical and Actual Plates Required vs. Relative Volatility for Methyl Ethyl Ketone from Ethanol Separation

| Relative Volatility | Theoretical Plates Required At Total Reflux, 99% Purity | Actual Plates Required, 75% Efficiency |
|---|---|---|
| 1.3 | 34 | 46 |
| 1.4 | 26 | 35 |
| 1.65 | 19 | 26 |

OBJECTIVE OF THE INVENTION

The object of this invention is to provide a process or method of extractive distillation that will enhance the relative volatility of methyl ethyl ketone from ethanol in their separation in a rectification column. It is a further object of this invention to identify effective extractive distillation agents that are stable and can be recycled.

SUMMARY OF THE INVENTION

The objects of this invention are provided by a process for the separation of methyl ethyl ketone from ethanol which entails the use of certain organic compounds when employed as the agent in extractive distillation.

DETAILED DESCRIPTION OF THE INVENTION

I have discovered that certain organic compounds will effectively increase the relative volatility between methyl ethyl ketone and ethanol during rectification when employed as the agent in extractive distillation. Those that remove the methyl ethyl ketone as overhead are isopropyl acetate, dimethyl adipate, dimethyl carbonate, methyl benzoate, butyl benzoate, hexyl formate, dimethyl phthalate, ethyl salicylate, 2-undecanone, 2-octanone, acetophenone, 3-methoxyacetophenone, 2-heptanone, 2,6-dimethyl-4-heptanone, phenetol, N,N-dimethylethanol amine, triethyl amine, salicylaldehyde, 1-(2-hydroxyethyl)-2-pyrrolidinone, phenol, N,N-dimethylacetamide, diethylene glycol methyl ether and nitromethane.

Those that remove the ethanol as overhead are ethylene glycol, 1,2-propanediol, 1,3-butanediol, 1,4-butanediol, triethylene glycol, diethylene glycol hexyl ether, polyethylene glycol 200, polyethylene glycol 300, polyethylene glycol 400, diethylene glycol, glycerol, tetraethylene glycol, 1,2,4-trimethylbutane, o-xylene, myrcene, p-cumene, morpholine, phenyl ether, butyronitrile, dipropyl amine, N,N-diethyl aniline, 2,6-diethyl aniline, 1,2-diaminocyclohexane, 2,6-diisopropyl amine, benzyl ether, benzyl cyanide, 1-nitropropane, benzonitrile, nitrobenzene, 2-nitrotoluene, nitroethane, 3-nitrotoluene, 1-methyl piperazine, formamide, N-methylpyrrolidinone, o-ethylaniline, acetonitrile, 2,4-dimethylphenol, 3-dimethylaminopropyl amine, 2-nitropropane, 3-Ethyl phenol and ortho tert.butyl phenol.

TABLE 3

Effective Extractive Distillation Agents For
Separating Methyl Ethyl Ketone From Ethanol

| Compounds | Relative Volatility |
| --- | --- |
| None | 1.1 |
| Isopropyl acetate | 1.35 |
| Dimethyl adipate | 1.55 |
| Dimethyl carbonate | 2.0 |
| Methyl benzoate | 2.0 |
| Butyl benzoate | 2.1 |
| Hexyl formate | 1.35 |
| Dimethyl phthalate | 1.45 |
| Ethyl salicylate | 1.85 |
| 2-Undecanone | 1.35 |
| 2-Octanone | 1.55 |
| Acetophenone | 1.5 |
| 3-Methoxyacetophenone | 1.55 |
| 2-Heptanone | 1.35 |
| 2,6-Dimethyl-4-heptanone | 1.35 |
| Phenetol | 1.5 |
| N,N-Dimethylethanol amine | 1.7 |
| Triethyl amine | 1.5 |
| 1-(2-Hydroxyethyl)-2-pyrrolidinone | 1.8 |
| Salicylaldehyde | 1.7 |
| Phenol | 1.8 |
| N,N-Dimethylacetamide | 1.5 |
| Diethylene glycol methyl ether | 1.4 |
| Nitromethane | 1.8 |

TABLE 4

Effective Extractive Distillation Agents For
Separating Ethanol From Methyl Ethyl Ketone

| Compounds | Relative Volatility |
| --- | --- |
| None | 1.1 |
| Ethylene glycol | 2.0 |
| 1,2-Propanediol | 1.6 |
| 1,3-Butanediol | 1.7 |
| 1,4-Butanediol | 1.8 |
| Diethylene glycol hexyl ether | 1.8 |
| Triethylene glycol | 1.7 |
| Polyethylene glycol 200 | 1.6 |
| Polyethylene glycol 300 | 1.4 |
| Polyethylene glycol 400 | 1.45 |
| Diethylene glycol | 1.65 |
| Glycerol | 2.0 |
| Tetraethylene glycol | 1.45 |
| 1,2,4-Trimethylbutane | 1.4 |
| o-Xylene | 1.4 |
| Myrcene | 2.0 |
| p-Cumene | 1.4 |
| Morpholine | 1.5 |
| Phenyl ether | 1.5 |
| Butyronitrile | 1.65 |
| Dipropyl amine | 1.45 |
| N,N-Diethyl aniline | 1.45 |
| 2,6-Diethyl aniline | 1.55 |
| 1,2-Diaminocyclohexane | 2.0 |
| 2,6-Diisopropyl amine | 1.5 |
| Benzyl ether | 1.45 |
| Benzyl cyanide | 1.7 |
| 1-Nitropropane | 1.6 |
| Benzonitrile | 1.7 |
| Nitrobenzene | 1.6 |
| 2-Nitrotoluene | 1.8 |
| Nitroethane | 2.0 |
| 3-Nitrotoluene | 1.8 |
| 1-Methyl piperazine | 1.5 |
| Formamide | 1.7 |
| N-Methyl pyrrolidinone | 1.4 |
| o-Ethyl aniline | 1.5 |

TABLE 4-continued

Effective Extractive Distillation Agents For
Separating Ethanol From Methyl Ethyl Ketone

| Compounds | Relative Volatility |
| --- | --- |
| 2,4-Dimethyl phenol | 1.7 |
| Acetonitrile | 1.4 |
| ortho tert. Butyl phenol | 2.0 |
| 3-Ethyl phenol | 1.4 |
| 3-Dimethylaminopropyl amine | 2.0 |
| 2-Nitropropane | 1.8 |

THE USEFULNESS OF THE INVENTION

The usefulness of this invention can be demonstrated by referring to the data presented in Tables 1, 2, 3 and 4. All of the successful agents show that methyl ethyl ketone can be separated from ethanol by means of extractive distillation in a rectification column and that the ease of separation as measured by relative volatilty is consiserable.

WORKING EXAMPLES

1. Fifty grams of a methyl ethyl ketone—ethanol mixture were charged to a vapor-liquid equilibrium still and refluxed for two hours. The overhead composition was 58.9 methyl ethyl ketone and the ethanol was 41.1%; the bottoms composition was 59.5% methyl ethyl ketone and the bottoms was 59.5% methyl ethyl ketone and 40.5% ethanol. This is a relative volatility of 2. The agent was methyl benzoate. 2. Fifty grams of ethanol—methyl ethyl ketone and fifty grams of glycerol were charged to a vapor-liquid equilibrium still and refluxed for two hours. The vapor composition was 55.9% ethanol and 44.1% methyl ethyl ketone; the bottoms composition was 61.3% ethanol, 38.7% methyl ethyl ketone. This is a relative volatility of 2.

I claim:

1. A method for recovering methyl ethyl ketone from a mixture of methyl ethyl ketone and ethanol which consists essentially of distilling a mixture consisting of methyl ethyl ketone and ethanol in the presence of an extractive distillation agent, recovering the methyl ethyl ketone as overhead product and obtaining the ethanol and the extractive distillation agent as bottoms product, wherein said extractive distillation agent consists essentially of one material selected from the group group consisting of nitromethane, isopropyl acetate, dimethyl adipate, dimethyl carbonate, methyl benzoate, butyl benzoate, hexyl formate, dimethyl phthalate, ethyl salicylate, 2-undecanone, 2-octanone, acetophenone, 3-methoxyacetophenone, 2-heptanone, 2,6-dimethyl-4-heptanone, phenetol, N,N-dimethylethanol amine, triethyl amine, salicylaldehyde, 1-(2-hydroxyethyl)-2-pyrrolidinone, phenol, N,N-dimethylacetamide and diethylene glycol methyl ether.

2. A method for recovering ethanol from a mixture of ethanol and methyl ethyl ketone which consists essentially of distilling a mixture consisting of ethanol and methyl ethyl ketone in the presence of an extractive distillation agent, obtaining the ethanol as overhead product and obtaining the methyl ethyl ketone and the extractive distillation agent as bottoms product, wherein said extractive distillation agent consists essentially of one material selected from the group consisting of 2,4-dimethylphenol, ethylene glycol, 1,2-propanediol, 1,3-butanediol, 1,4-butanediol, triethylene glycol, diethylene glycol hexyl ether, polyethylene glycol 200, polyethylene glycol 300, polyethylene glycol 400, diethylene glycol, glycerol, tetraethylene glycol, 1,2,4-trimethylbutane, o-xylene, myrcene, p-cumene, morpholine, phenyl ether, butyronitrile, dipropyl amine, N,N-diethyl aniline, 2,6-diethyl aniline, 1,2-diaminocyclohexane, 2,6-diisopropyl amine, benzyl ether, benzyl cyanide, 1-nitropropane, benzonitrile, nitrobenzene, 2-nitrotoluene, nitroethane, 3-nitrotoluene, 1-methyl piperazine, formamide, N-methylpyrrolidinone, o-ethylaniline, acetonitrile, 3-dimethylaminopropyl amine, 2-nitropropane, 3-ethyl phenol and ortho tert, butyl phenol.

* * * * *